United States Patent
Visser et al.

(12) 
(10) Patent No.: US 6,600,093 B1
(45) Date of Patent: Jul. 29, 2003

(54) POTATO PLANT PRODUCING ESSENTIALLY AMYLOSE-FREE STARCH

(75) Inventors: Richard Gerardus Franciscus Visser, Bennekom (NL); Evert Jacobsen, Wageningen (NL); Willem Jan Feenstra, Haren (NL)

(73) Assignee: Cooperatieve Verkoop-en Productievereniging van Aardappelmeel en Derivaten AVEBE B.A., Veendam (NL)

( * ) Notice: Subject to any disclaimer, the term of this patent is extended or adjusted under 35 U.S.C. 154(b) by 0 days.

(21) Appl. No.: 08/294,619

(22) Filed: Aug. 23, 1994

Related U.S. Application Data (63) Continuation of application No. 08/159,714, filed on Dec. 1, 1993, now abandoned, which is a continuation of application No. 07/835,886, filed on Feb. 14, 1992, now abandoned.

(51) Int. Cl.$^7$ .................. C12N 15/82; C12N 15/84; C12N 15/29; A01H 5/00; C12P 19/04
(52) U.S. Cl. ............... 800/317.2; 800/278; 800/284; 800/286; 800/287; 800/288; 800/294; 435/101; 435/468; 435/469; 536/23.6; 536/24.5
(58) Field of Search ............... 435/172.3, 101, 435/468, 469; 800/205, DIG. 42, 278, 286, 287, 288, 284, 317.2, 294; 536/24.1, 24.5, 23.2, 23.6

(56) References Cited

PUBLICATIONS

Rohde et al. 1990. J. Genet. & Breed. 44(4): 311–315.*
Visser et al. 1991. Mol. Gen. Genet. 225:289–296.*
Visser, R. 1989, PhD Thesis.*
Hergersberg, M. 1988, PhD Thesis.*
Hovenkamp–Hemelink et al.; Theor Appl Genet (1987) 75:217–221 Isolation of an amylose–free starch mutant of the potato.
Shure et al.; vol. 35. 225–233; Nov. 1983; Molecular (*Cell*) Identification and Isolation of the Waxy Locus in Maize.
Hergersberg; 1988; pp1–81; Molekular Analyse des waxy Gens aus Solanum tuberosum und Expression von waxy antisense . . . .
Visser; 1989; pp 1–141; Manipulation of the Starch Composition of Solanum Tuberosum L. Using agrobacterium . . . (PhD Thesis).
Visser et al.; Theor Appl Genet; 1989; 78:594–600; Efficient transformation of potato (Solanum Tuberosum L.) using a . . . .
Visser et al.; Theor Appl Genet (1989) 78:705–714; Expression and inheritance of inserted markers in binary . . . .
Krol et al.; Nature vol. 333; 1988; An anti–sense chalcone synthase gene in transgenic plants inhibits flower . . . pp 866–869.
Smith et al., Nature vol. 334; 1988; Antisense RNA inhibition of polygalacturonase gene expression in transgenic tomatoes pp 724–6.
Benfey et al.; The EMBO Journal vol. 8 No. 8; pp 2195–2202; 1989; The CaMV 35S enhancer contains at least two . . . .
Delauney et al.; Proc. Natl. Acad. Sci. USA; vol. 85; pp 4300–4304; 1988; A stable bifunctional antisense . . . .
Leij et al.; Theor Appl Genet; 1991; 82: 289–295; Complementation of the amylose–free starch mutant of potato . . . .
Schuch et al.; Plant Molecular Biology 13:303–311; 1989; Control and manipulation of gene expression during tomato fruit . . . .
Sheehy et al.; Proc,. Natl. Acad. Sci. USA; vol. 85; pp 8805–8809; 1988; Reduction of polygalacturonase activity . . . .
Visser et al.; Plant Molecular Biology 12:329–337; 1989 Transformation of homozygous diploid potato with an . . . .
Visser et al.; Plant Science; 64 (1989) 185–192; Molecular Cloning and Partial Characterization of the Gene for . . . .
Visser; Plant Tissue Culture Manual B5: 1–9, 1991; Regeneration and transformation of potato by Agrobacterium tumefaciencs.
Visser et al.; Mol Gen Genet (1991) 225:289–296; Inhibition of the expressin of the gene for granule–bound starch . . . .
Visser et al.; Plant Molecular Biology; 17:691–699; 1991 Expression of a chimaeric granule–bound starch synthase–GUS . . . .

* cited by examiner

*Primary Examiner*—David T. Fox
(74) *Attorney, Agent, or Firm*—Steptoe & Johnson LLP; D. Douglas Price (57) ABSTRACT

A potato plant which has a genome containing, as a result of genetic engineering, at least one gene construct containing a potato granule-bound starch synthase (PGBSS) cDNA or genomic DNA sequence in reverse or functional orientation in an expression cassette which is functional in potato plants, the gene construct giving rise to tubers containing essentially amylose-free starch. In one embodiment, the gene construct contains a PGBSS cDNA sequence in reverse orientation which results in the production of PGBSS antisense RNA.

23 Claims, 5 Drawing Sheets

```
     AAGCTTTAACGAGATAGAAATTATAATACTCCGTTTGTTCATTACTTAACAAATGCAACAGTATCTTGTAC
-1073
-1000 CAAATCCTCCTCTCTTTCAAACTTTTCTATTGGCTGTTGACAGAGTAATCAGGATACAAACCACAGTATTTAATTGACTCATCCACCAGATATTATGA
 -900 TTTATGAATCCTCGAAAAGCCTATCCATTAAGTCCTCATCTCTATGGATATACTTGACAGTTTCTTCCTATTGGGTTTTTTTTTCCTGCCAAGTGGAAC
 -800 GGAGACATGTTATGTTGTATACGGGAATCTCGTTAAAAAAAAAAAATACAATAGGAACAATGTAACAAACATTGAATGTTGTTTTAACCATCCTTCCTT
 -700 TTAGCAGTGTATCAATTTTGTATAGAACCATGCATCTCAATCTTCATCTTAATACTAAAAAATGCAACAAAATTCTAGTGGAGGGACCAGTACCAGTACATTAGA
 -600 TATTATTTTTATTACTATAATAATATTTTAATTAACACGAGACATAGGAATGTCAAGTGGTAGCGGTAGGGAGTTGGTTAGTTTTTAGATACTAG
 -500 GAGACAGAACCGGAGGGGCCCATTGCAAGGCCCAAGTTGAAGTCCAGGTGAATCAACAAAGAGAGGGCCCATAATACTGTCGATGAGCATTTCCTAT
 -400 AATACAGTGTCCACAGTTGCCTTCCGCTAAGGATAGCCACCCGCTATTCTCTTGACACGTGTCACTGAAACCTGCTACAAATAAGGCAGGCACCTCTC
 -300 ATTCTCACACTCACTCACACAGGCTCAAACAAGTGgtaacttttactcatctctattatttctgatttcatgcatgtttcccacattctattatgaa
 -200 tcgtgttatggtgtataaacgttgttcatatctcatctcatctctgatttgattctcctgcctactgtaatcggtgataaatgtgaatgcttcct
 -100 cttcttcttcttcttcttcagaaatcaattcgttttgttttgttcatcgtagGTTGGTAGATTCCCTTTTGTAGACCACACATCAC
    1 ATGGCAAGCATCACAGCTTGTGTCAACAGCTTCACACCACTTGTGTCAAGAAGCCAAATCAACTTGTCACAGATAGGACTCAGGAACCATACTC
  101 TGACTCACAATGGTTAAGGGCTTGATGGCTCCAATCAAGAACTAATACTAAGGTAACACCCAAGATGGCATCCAGAACTGAGACCAA
  201 GAGACCTTGGATGCTCAGCTACCATTGTTTGTGGAAAGGAATGAACTTGATCTTTGTGGGTACTGAAGGTTGGTCCTTGGAGCGAAAACTGGTGGACTAGGT
  301 GATGTTCTTGCTGGACTACCACCAGCCCTTGCAgtaagtcttcattggttacctactcattcattctttattttgttgttagtttctactgcatca
  401 gtctttttatcattagGCCCGCGGACATCGGGTAATGACAATATCCCCCGTTATGACCAATACAAAGATGCTTGGGATACTAGCGTTGCGGTTGAGgt
  504 acatcttcctatttgatacggtacaatattgttccctcagaatgtgatccgctacttttatctgcagtCAAAGTTGGAGACAGC
  601 ATTGAAATTGTTGCTTGTTCTTCACTGCTATAAACGTGGGGTTGACCTGTGTTTTTGTTGACCACCCAATGTTCTTGGAGAAAgtaagtaagcatattatga
  701 ttatgaatccgtcctgagggatacgcagaacaggtcatttgaatatcttttaactcttactggtgcttttactcttttaagGTTGGGGCAAACTGGT
  801 TCAAAAATCTATGGCCCCAAAGCTGGACTAGATTATCTGGACAATGAACTTAGGTTCAGCTTGTTGTGTCAAgtaagttagttactgtatactgttgt
  901 cttgattttatgtggcatttgtCtgtaattaacacatccctagttttttaacctgtttttcttctcagCAGCCCTAGAGGCACCTAAAGTTTTGAACAGTAGCAAC
 1001 TACTTCTCAGGACCATATGgtaattaacacatccctagtatatcattgtaggtaatatcatcttatttgccattcctgcagG
 1101 AGAGGATGTTCTCTCATTGCCAATGATTGGCACACAGCTCTCATTCCTTGCTACTTGAAGTCAATGTACCAGTCCAGAGAATCTATTTGAATGCCAAG
 1201 gtaaaattttcttgtattcacttgattgcgtttaccctgcaaatcagtaagtttgtattaataatgataatttcacattgcctccagTCGCTTTCT
 1301 GCATCCATAACATTGCCTACCAAGGCCGATTTCTTTCTCTGACTTCTTCAATCTTCCTGATGAATTCGTGATCTGATCATTCATTGATGG
```

FIG. 3B

```
1401  gtatgtatttaatgcttgaaatcagaccaccaacttttgaagctcttttgatgctagtagttgagtttaaaatttttgcagATGAGAAGCCTGTTA
1501  AGGGTAGGAAAATCAACTGGATGAAGGCTGGGATATTAGAATCACATAGGGTGGTTACAGTGAGCCCATACTATGCCAAGAACTTGTCTCTGCTGTTGA
1601  CAAGGGTGTTGAATTGGACAGTGTCCTTCGTAAGACTTGCATAACTGGGATTGTGAATGGCATGGATACACAAGAGTGGAACCCAGGACTGACAAATAC
1701  ACAGATGTCAAATACGATATAACCACTgtaagataagatttttccgactccagtatatgctaaattgttgttttgtatgtttatgaaattaaagagttcttgc
1801  taatcaaaatctctatacagGTCATGGACGCAAAAACCTTTACTAAAGGAGGCTCTTCAAGCAGCAGTTGGCTTGCCTGTTGACAAGAGATCCCTTTGAT
1901  TGGCTTCATCGGCAGACTTGAGGAGCAGAAAGGTTCAGATATTCTTGTTGCTGCAATTCACAAGTTCATCGGATGTTCAAATTGTAGTCCTTgta
2001  agtaccaaatggactcatggtatctctctgttgagtttactgttgtgccgaaactgaaattgacctgctactcatcctatgcatcagGGAACTGGCAAAAA
2101  GGAGTTTGAGCAGGAGATTGAACAGCTCGAAGTGTTGTACCCTAACAAAGCTAAAGGAGTGGCAAAATTCAATGTCCCTTGGCTCACATGATCACTGCT
2201  GGTGCTGATTTTATGTTGGTTCCAAGCAGATTGAACCTTGTGGTCTCATTCAGTACATGCTATGCGATATGGAACAgtaagaaccataagagcttgta
2301  cctttttactgtgagtttaaaaaagaatcataagacctttgttttccgtctaaagtttaatagccaactaaatgttactgcagcaagctttcatttctga
2401  aaattggttatctaattttaacataatcacatgtgagtcagTGCCAATCTGTGCATCGACTGGTGGACTTGTTGACACTGTGAAAGAAGGCTATACTGG
2501  ATTCCATATGGGAGCCTTCAATGTTGAAGtatgtgatttttacatcaattgtgtacttgtacatggtccattctcgtcttgatatcccctttgttgcataa
2601  acattaacttattgcttcttgaattggttagTGCGATGTTGTTGACCCAGCTGATGTGCTTAAGATAGTAACAACAGTTGCTAGAGCTCTTGCAGTCTA
2701  TGGCACCCTCGCATTTGCTCGAGATGATAAAAAAATTGCATGTCAGAGGAACTCTCCTGGAAGgtaggtgtcaaattgataatttgcgtaggtacttcagtt
2801  tgttgttctcgtcagtactgatggatgccaactggttgttcatgcagGAACCTGCCAAGAAATGGGAGAGACATTGCTATTGGGCTTAGGAGCTTCTGCCAGT
2901  GAACCCGGTGTTGAAGGGAAGAAATCGCTCCACTTGCCAAGCCTATTGTAGCCACTCCCTAAATGAGCTTTGGTTATCCTTGTTCAACATAAGATCA
3001  TTAAGCAAACGTATTTACTAGGAACTATGTAGAACCTATTATGGGTCTCAATCATCTACAAAATGATTGGTTTTGCTGGGGAGCAGCAGCATATTA
3101  GGCTGTAAATCCTGGTTAATGATTTTGTAGGTAAGGGCTATTAGGTGTGTGGATCAAAGTCAATAGAAAATAGTTATTACTAAGCTTGCAACTAA
3201  ATACTTAGTAATGTAGCATAAATATACTAGTAATAATATATATGCGTAATTTGTTGTACCTTTTCTTGCATAATTATTTGCAGTACATATATAATGA
3301  AAATTACCCAAGAATCAATGTTTCTTGCTCCGTCCTCCTTGATGATTTTTACTCAATGCAGAGCTAGTGTGTTAAGTATAAATTTGTTAAAAGA
3401  AGTAATCAATTTCAAATTAGTTGGTTCATATGAAAGAAGCTGGCAACTTTGAGGAGATGGCTATTGAAGTTCAAAGTGATTATGTGAAAACA
3501  ATGCAACATTTATGTCAATCAACACTTAAATTATTGCATTTAGAAAGATATTTTTGAGCCCACGACATTCATTCATAAAGTAAGGTAG
```

POTATO PLANT PRODUCING ESSENTIALLY AMYLOSE-FREE STARCH

This application is a continuation of application Ser. No. 08/159,714, filed Dec. 1, 1993, abandoned, which is a continuation of application Ser. No. 07/835,886, filed Feb. 14, 1992, abandoned.

FIELD OF THE INVENTION

The invention is in the field of genetic engineering by recombinant DNA technology, more particularly the genetic engineering of potato plants in order to change the starch composition in the tubers towards essentially amylose-free starch.

BACKGROUND OF THE INVENTION

Starch is the major storage carbohydrate in potato and consists of two components, a linear (1→4)α-D-glucan polymer and a branched (1→4) (1→6)α-D-glucan called amylose and amylopectin, respectively. Amylose has a helical conformation with a molecular weight of $10^4$–$10^5$. Amylopectin consists of short chains of α-D-glucopyranose units primarily linked by (1→4)α bonds with (1→6)α branches and with a molecular weight up to $10^7$. In plants starch is found in two types of plastids: chloroplasts and amyloplasts. In both types of organelles the starch occurs as granules. In chloroplasts so-called transitory starch is accumulated for only a short period of time, whereas starch in amyloplasts is accumulated for long term storage and hence is named reserve starch. Generally, amylose makes up 11%–37% of the total reserve starch and variation in the amylose content is not only found among different plant species, but also among different cultivars of the same species. In potato the amylose content in the tuber varies from 18% to 23%. Furthermore, in a number of plant species mutants are known with a starch composition which deviate significantly from the above mentioned percentages.

Transitory and reserve starch are generally considered to be synthesized by the same enzymes. Starch metabolism in leaves follows a diurnal rhythm: synthesis and accumulation occur during the light period while hydrolysis occurs during the night. In storage tissue, starch synthesis occurs during a specific phase of tissue development; the synthesis being the predominant function of amyloplasts. The amount of amylose found in storage tissue of potato is about twice as high as that in leaves.

Sucrose is considered to be the major substrate for starch biosynthesis which involves the following steps: initiation, elongation, branching and granule formation. In the pathway of conversion of sucrose into amylose and amylopectin at least 13 enzymes play a role. Three groups of enzymes are directly involved in the formation of starch. These enzymes are phosphorylase, starch synthases and branching enzymes. Phosphorylase is active in starch breakdown, branching enzyme converts amylose into amylopectin by the breakage of (1→4)α-bonds and the synthesis of (1→6)α-bonds. Starch synthases are responsible for the synthesis of starch by the addition of ADP (UDP) glucose subunits to the non-reducing end of an (1→4)α-D-glucan polymer. Starch synthase has been identified in two forms: one form is soluble while the other is tightly associated with starch granules. The soluble enzyme uses only ADP-glucose as the D-glucosyl donor, whereas the granule bound starch synthase (GBSS) utilizes ADP-glucose and UDP-glucose. Solubilization of the GBSS protein from starch granules of various plants has been reported. Although in maize there are thought to be at least two forms of GBSS, potato seems to have only one form. The presence and activities of the different starch synthases are important to starch biosynthesis not only because they have an effect on the amylose/amylopectin ratio in starch, but also because they can have a large impact on total starch content. In general, it appears that complete suppression of the enzymes producing amylose can be achieved with almost no change in the total amount of starch laid down, whereas suppression of the enzyme system producing amylopectin leads to a marked decrease of the amount of total starch.

Starch as such or in modified form is widely used in the food, paper and textile industries. With the depletion of natural oil resources starch could also become a substitute for oil as a raw material for the chemical industry. Therefore, it could become of major interest to produce starch which meets special requirements for certain applications. Although special forms of starch are already available from mutants of maize and rice and starches from other sources might have certain advantages, genetical engineering could be an option in order to obtain tailor-made starches in plants in which (recessive) mutants are not easily obtained. Selection of mutants is especially difficult in vegetatively propagated crops which are mainly crosspollinators and/or polyploids, such as the potato.

Although recently in a laborious isolation procedure a mutant of potato (amf) was isolated which, in analogy to the wx mutants in maize, lacks GBSS protein, GBSS activity and amylose (Hovenkamp-Hermelink et al. 1987), the breeding of such a mutant into a cultivar will take another number of years. One cause for the long duration of the procedure is the fact that a haploid clone had to be used for the isolation of the recessive mutant. To circumvent problems of isolating recessively inherited mutants in a polyploid crop like potato and to speed up the introduction of such a mutant character in potato varieties, the antisense approach would be a very important alternative, because an antisense gene would act as a dominant suppressor gene. The great advantage is that eventually it will become possible to mimick such a mutant phenotype directly in a tetraploid variety. With the availability of GBSS sequences, both from maize (Shure et al 1983) and potato (Hergersberg 1988; Visser et al 1989d) and an efficient transformation system for potato (Visser et al 1989a, 1989b) this approach could be tested.

It has been shown that antisense RNA transcripts can be used to mimic mutations in pro- and eukaryotes (for review see van der Krol et al. 1989). Antisense RNA was originally found as a naturally occurring mechanism used to control gene expression in bacteria (Tomizawa et al. 1981; Mizuno et al. 1984). Izant and Weintraub (1984, 1985) proposed that antisense RNA could be used to inhibit the expression of eukaryotic genes. By inhibiting the expression of specific target RNAS, this approach has led to the generation of mutant phenotypes in a number of different eukaryotic systems. In plants the use of antisense RNA proved to be successful in effectively inhibiting the activity of nopaline synthase (Rothstein et al. 1987; Sandler et al. 1988), chloramphenicol acetyltransferase (Ecker and Davis 1986; Delauney et al. 1988), chalcone synthase (van der Krol et al. 1988), polygalacturonase (Smith et al. 1988; Sheehy et al. 1988), phosphinotricin acetyl transferase (Cornelissen and Van de Wiele 1989) and β-glucuronidase (Robert et al. 1989).

Visser (1989) tested whether the antisense approach could be used to inhibit the expression of the gene for granule-bound starch synthase in potato using heterologous antisense constructs, i.e. an antisense gene constructed from a maize genomic GBSS gene.

The antisense gene was fused between the 35S cauliflower mosaic virus promoter and the nopaline synthase terminator in the binary vector pROK-1, which also carries a plant selectable kanamycin resistance gene. Since it was known from the amf-mutant that the mutation is expressed in all tissues in which starch is formed, including columella cells of the root cap, it was expected that also antisense effects would be visible in roots. The presence or absence of amylose could be easily detected because amylose forms a blue staining complex with the iodine present in Lugol's solution (I—KI). Starch without amylose, i.e. only containing amylopectin, forms a reddish-brown staining complex with iodine. In order to efficiently test the introduced antisense gene in potato for a biological effect a transformation system was developed in which the binary antisense vector was incorporated into *Agrobacterium rhizogenes*. The binary vector was present next to the wildtype Ri-plasmid of *A. rhizogenes* which is responsible for the formation of so-called hairy roots on plant explants. *Agrobacterium rhizogenes* was used instead of *Agrobacterium tumefaciens* because it is possible to screen for an effect of the introduced constructs already after 10 days by staining hairy roots with Lugol's solution and because plants can be easily regenerated from hairy roots. In this way heterologous (maize) binary antisense GBSS plasmids were transferred by *A. rhizogenes* to stem segments from potato.

Both in untransformed or otherwise transformed wildtype roottips never anything else than blue staining roottips were present. Hairy roots obtained after transformation with *A. rhizogenes* carrying heterologous binary antisense GBSS plasmids were analyzed for the presence or absence of amylose in their starch by staining the roottips with Lugol's solution. The majority of the roots stained blue as wildtype untransformed roots did. However, some roots (1–15% of the stained roots) had a color pattern different from that of wildtype roots in that the central cells of the root cap were blue and the cells towards the outside of the rootcap were red. These intermediate colouring roots were indications that the inserted antisense genes had some effect on the amylose content. Root clones were established and subcultured and roottips were investigated every fortnight during six weeks of culture. The results of these experiments showed that instability of color patterns occurred at a rather high frequency. The instability of the effect in columella cells was the reason to regenerate plants from kanamycin resistant hairy roots irrespective of their color.

Figure 2A:
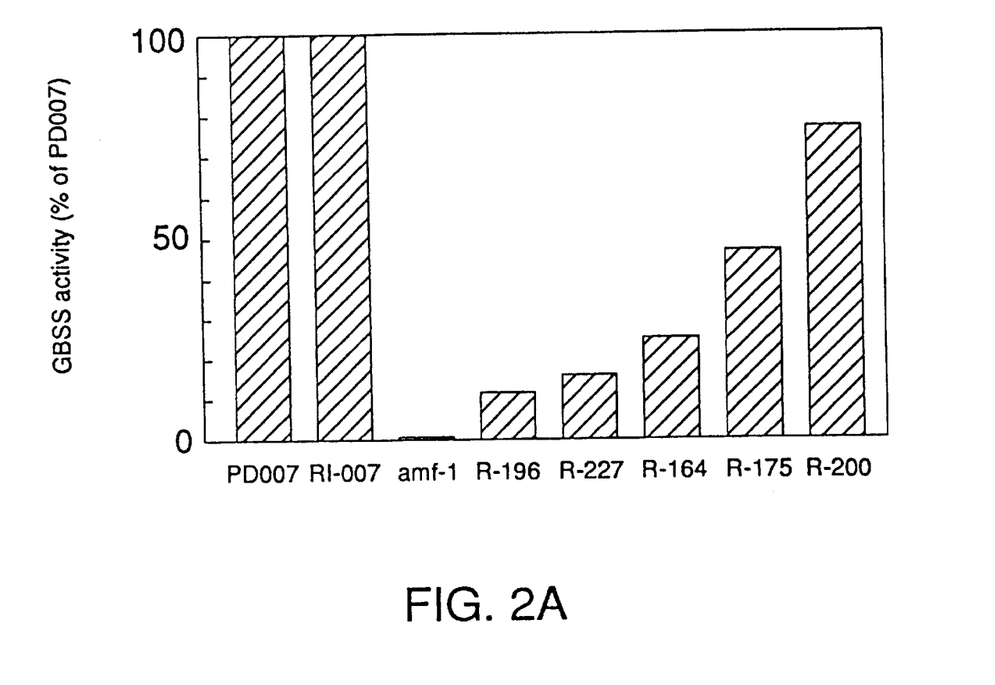
FIGS. 2A–2D compare the antisense effects on GBSS activity and amylose content of tuber starches in the case of heterologous constructs (2A, 2B) and homologous constructs (2C, 2D).
Figure 2B:
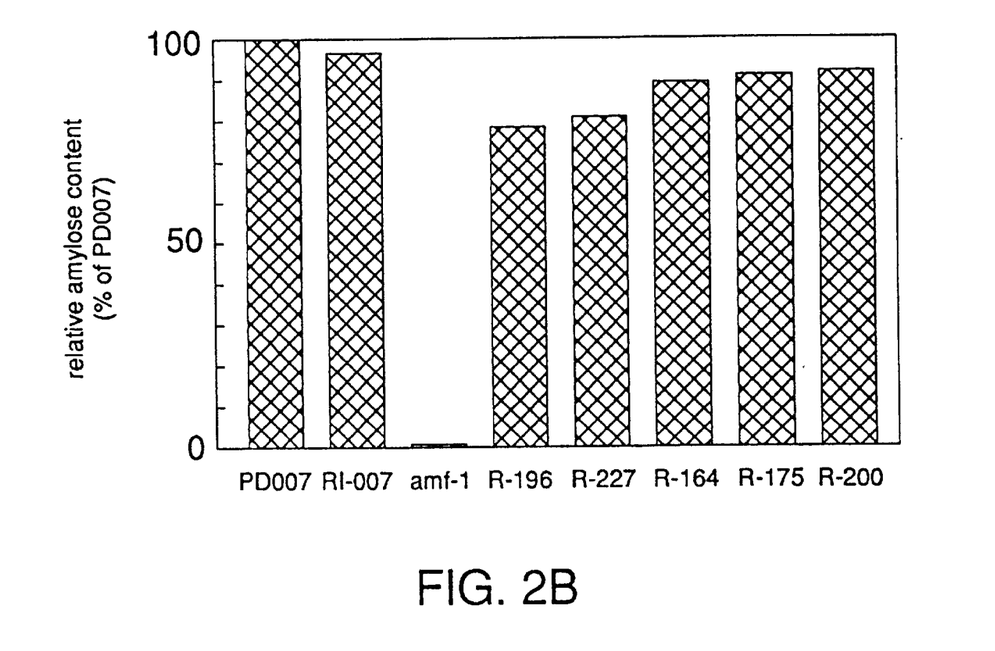

On plants, regenerated from kanamycin resistant hairy roots, microtubers as well as soil grown tubers were induced. Analysis of these tubers showed that none of them had red or intermediate staining starch. All tubers showed blue staining (=amylose containing) starch. Starch isolated from these tubers was analyzed for the presence of GBSS protein and GBSS activity and for the presence of amylose. In all tubers tested GBSS protein was, seemingly unaltered, present. However, GBSS activity in particular and to a much lesser degree amylose content were affected in starch preparations from a number of transformed plants. As shown in FIG. 2A, the untransformed wildtype (PD007) and a pBI121 transformed wildtype (Ri-007) had similar GBSS activities, while the amf-mutant had no detectable GBSS activity. GBSS activity was inhibited significantly in the antisense GBSS transformants down to only 10% of that found in wildtype plants. Total inhibition of GBSS activity was not obtained in any of the transformants analyzed. The amylose content measurements gave a different picture. Although in almost all cases there was a somewhat lower amylose content, the difference was significant in only two cases (R-196 and R-227, FIG. 2B). The maximum reduction of the amylose content was found in transformant R-196, which also had the lowest GBSS-activity; a reduction down to 78% of the wildtype amylose content. Molecular analyses of the antisense transformants revealed that the number of integrated antisense copies was 1 to 4, but only those plants which contained three or more copies of the antisense GBSS construct showed a pronounced effect on GBSS activity. It is evident from these observations that the effect of a lower GBSS activity on the amylose/amylopectin ratio is not straightforward.

The results described resemble very closely the situation obtained in tomato when using antisense poly-galacturonase genes. A reduction of 90% of the polygalacturonase activity does not have a great effect on the lycopene content (Sheehy et al. 1988, Smith et al. 1988).

The above results were not too encouraging, but it was nevertheless decided to expand the investigations to homologous constructs derived from a full-length potato GBSS cDNA.

Surprisingly, it was found that it is possible to inhibit the expression of granule-bound starch synthase (GBSS) in potato, and thus affect the amylose content of potato tuber starch, by stably introducing homologous antisense constructs. The results described show that it is possible using the antisense approach to interfere with enzymes in biosynthetic pathways such as starch biosynthesis. In using this technique loss of function mutations, such as the amf mutation, which are principally inherited recessively can be mimicked, because antisense genes act as dominant (hemizygous) genes suppressing translation of mRNA.

Surprisingly, it was subsequently found that the effect of essentially amylose-free tuber starch could also be obtained by stably introducing homologous sense constructs, e.g. based on potato GBSS genomic DNA. A phenomenon known as co-suppression appears to occur; it is not yet possible to give an explanation of it.

SUMMARY OF THE INVENTION

The invention provides a potato plant which has a genome containing, as a result of genetic engineering, at least one gene construct containing a potato granule-bound starch synthase (PGBSS) cDNA or genomic DNA sequence in reverse or functional orientation in an expression cassette which is functional in potato plants, said gene construct giving rise to tubers containing essentially amylose-free starch.

In one preferred embodiment, said gene construct contains a PGBSS cDNA sequence in reverse orientation which results in the production of PGBSS antisense RNA.

In another preferred embodiment, said gene construct contains a PGBSS genomic DNA sequence in functional orientation which results in co-suppression of PGBSS enzyme activity.

The invention further provides cells, parts and tubers of said potato plant, and essentially amylose-free starch from it.

DETAILED DESCRIPTION OF THE INVENTION

The invention will be illustrated by means of examples which are given for illustrative purposes only and may not be construed as limiting the scope of the invention. For example, the transformation system used in example 1

(*Agrobacterium rhizogenes*) may be replaced by any suitable alternative, such as the *Agrobacterium tumefaciens* transformation system (see ex. 2) or the direct gene transfer technique (DGT). Such alternatives are well known to the person skilled in the art. A survey of transformation systems suitable for potato is given in chapter I of Visser (1989).

Similar remarks apply to the choice of the transformation vector (if any), the elements of the expression cassette, the selection markers, etc. For example, the PGBSS promoter may be used to regulate the transcription of the sense or anti-sense PGBSS DNA, instead of the CaMV promoter used in example 1. The sense or anti-sense PGBSS cDNA or genomic DNA sequence does not have to cover the complete coding sequence but should cover a sufficient part of it to be effective for obtaining tubers containing essentially amylose-free starch. At present, the use of anti-sense PGBSS cDNA is preferred above using anti-sense PGBSS genomic DNA. The gene construct used may contain the PGBSS DNA (preferably genomic DNA) in its functional orientation and yet result in essentially amylose-free tuber starch.

DESCRIPTION OF THE DRAWINGS

FIG. 1 shows the construction of the sense and antisense granule-bound starch synthase (GBSS) vectors. The original GBSS cDNA which contained an internal EcoRI site was subcloned as two fragments in pUC9, denoted pWx 1.1 and pWx 1.3. The 1.3 kb GBSS cDNA fragment from pWx 1.3 was ligated into the partial EcoRI-restricted plasmid pWx 1.1 yielding pGB2. Plasmid pGB2 was restricted with SpeI, made blunt ended with Klenow enzyme, BamHI linked and restricted with BamHI. The GBSS cDNA fragment was ligated into BamHI-restricted pUC18 yielding pGB6 and into BamHI-digested calf intestinal phosphatase (CIP) treated pROK-1 yielding pGB50 (antisense) and pGB60 (sense). Abbreviations: B, BamHI; E, EcoRI; H, HindIII; S, SpeI; LB, RB, left and right T-DNA border repeats; Km$^r$, kanamycin resistance marker expressed at bacterial level; NPT-II (neomycin phosphotransferase II gene) kanamycin resistance marker expressed at plant level; $P_{CaMV}$, 35S cauliflower mosaic virus promoter; $T_{NOS}$, nopaline synthase terminator.

2A. GBSS activities of control (PD007, Ri-007 and amf) potato and antisense transformed potato tuber starches.
GBSS activity of wildtype PD007: 86.2 pMol ADP glucose min$^{-1}$ mg starch$^{-1}$ GBSS activity of mutant amf: 1.3 pMol ADP glucose min$^{-1}$ mg starch$^{-1}$.

2B. Apparent amylose content of control potato and anti-sense transformed potato tuber starches
wildtype PD007: 18.4%
mutant amf: 0%

2C. GBSS activity of control (PD007, Ri-007 and amf) potato and class I (WA 501, WA 511), class II (WA 504) and class III (WA 507, WA 514) antisense transformed tuber starches.
wildtype PD007: 66.9 pMol ADP glucose min$^{-1}$ mg starch$^{-1}$
mutant amf: 0 pMol ADP glucose min$^{-1}$ mg starch$^{-1}$ 2D. Apparent amylose content of control and antisense transformed potato tuber starches
wildtype PD007: 20.3%
mutant amf: 0%

EXAMPLE 1

Materials and Methods
Cloning the Potato GBSS Gene (Visser et al. 1989)
The *Solanum tuberosum* clones H7322 (AM 79.7322, 2n=x=12), 86.040 (amylose-free mutant amf-1, 2n=x=12, derived after a mutagenic treatment of H7322 leaf strips (Hovenkamp-Hermelink et al., Theor. Appl. Genet., 75:217–221 (1987)), 87.1030/14 (2n=2x=24 and 87.1029/15 amylose free F2 plants 2n=2x=24 (Jacobsen et al., *Euphytica* (1989)) were used as source for RNA and DNA isolation. The plants were grown in greenhouse at 18° C./16° C. day/night temperature and 16 h light.

Genomic Library Construction
DNA was isolated from young H7322 and 86.040 potato leaves and cesium chloride purified according to Schwartz-Sommer et al. (Schwarz-Sommer et al., *Embo J.*, 3:1021–1028 (1984)). The genomic libraries were constructed essentially as described by Maniatis et al. (Maniatis et al., Cold Spring Harbor, N.Y. (1982)). Briefly, potato DNA was partially digested with restriction enzyme MboI and size fractionated on a 0.7% agarose gel; fraction containing 14–22 kb fragments were cut out of the gel and isolated by electroelution in 1×TAE (40 mM Tris acetate, 1 mM EDTA). The electroeluted DNA was applied on a DE52 cellulose (Whatman) column, washed several times with TE (10 mM Tris-HCl, 0.1 mM EDTA, pH 7.4), eluted with 1 M NaCl, phenol extracted and precipitated with absolute ethanol. Phage λ EMBL4 DNA (Frischauff et al., *J. Mol. Biol.*, 170:827–842 (1983)) was digested with restriction enzymes BamHI and SalI and annealed in the presence of Mg$^{2+}$ as described by Maniatis et al. The DNA was fractionated onto a 10–40% potassium acetate density gradient (Maniatis et al.) and the purified EMBL4 arms were used in the ligation mixture.

EMBL4 DNA was ligated to the electroeluted size fractionated potato DNA, packaged and used to transfect *Escherichia coli* strain K 803 (Shure et al., *Cell*, 3:225–233 (1983). The genomic libraries were transferred to Nitrocellulose filters (Schleicher and Schull BA85 0.45 μM) and screened by plaque hybridization (Benton et al., *Science* 196:180 (1977)) to the random primed labelled (Feinberg et al. *Anal. Biochem.*, 132:6–13 (1983)) insert of the granule bound starch synthase cDNA clone pWx1.3(3'-end (Hergersherg, Thesis, Koln (1988)). Hybridizing plaques were purified by two further rounds of plaque hybridization and DNA was prepared form large scale liquid lystates as described in Maniatis et al.

Plant RNA Preparation
Total RNA was isolated from various tissues by grinding the frozen material to a fine power using a Waring blendor. To 1 g of powdered material, 4 ml (60° C.) extraction buffer (0.2 M NaAc, pH 8.5,1% SDS, 10 mM EDTA) and 2 ml phenol were added. After vigorous vortexing for 2 min, 2 ml chloroform was added. The tube was vortexed vigorously and transferred to a waterbath (60° C. for 5 min with occasional shaking. After centrifugation at 20 000×g for 30 min the aqueous phase was removed and extracted three times with phenol/chloroform and once with chloroform alone. The aqueous phase was made 2 M with LiCl and the RNA was allowed to precipitate for 4–12 h at 4° C. The RNA was collected by centrifugation for 10 min at 10 000×g, the resulting pellet washed twice with 70% ethanol and finally dissolved in $H_2O$. The RNA was again precipitated with ethanol after the addition of 1/10 volume of 3 M NaAc pH 5.0, centrifugated at 10 000×g, washed twice with 70% ethanol and dissolved in 100 μl of $H_2O$. The E260/E280 were measured and the RNA was stored at −20° C. Poly A+RNA was isolated using Hybond™mAP (messenger affinity paper Amercham International Plc, Amersham, U.K.) according to the manufacture instructions.

RNA and DNA Blot Hybridization

Total RNA and poly A+RNA were denaturated with formaldehyde and formamide and electrophoresed in 1% agarose gels (Maniatis et al.) At the end of the run the gel was soaked in $H_2O$ for 10 min and stained for 3 min. in 50 mM NaOH, 10 mM NaCl, 5 μg/ml ethidium bromide. Destaining was for 30 min. in 0.1 M Tris-HCl (pH 7.5). The RNA was transferred to Gene Screen Plus membranes (NEN) with 10×SSPE (0.1 $MNaH_2PO_4$, 1.5 M NaCl, 10 mM EDTA) and hybridized with random primed labelled (Feinbkerg et al.) GBSS cDNA. RNA dot blots were performed as described by White and Bancroft (White et al., *J. Biol Chem.* 257:8569–8572 (1982)) using Schizophyllum commune RNA as a negative control.

Plant DNA isolation for Southern blots was according to Dellaporta et al. (Dellaporta et al., *Plant. Mol. Biol. Rep.*, 1:19–21 (1983)). DNA was digested with the indicated restriction endonucleases, electrophoresed in 0.7% agarose gels using standard procedures (Maniatis et al.) and blotted onto Gene Screen Plus membrane according to the manufacturers instructions. Hybridizations of DNA blots were performed essentially as described (Visser et al., *Plant Mol. Biol.* 12:329–337 (1989)), (Visser et al. *Theor. Appl. Genet.* 76:420–424 (1988)). Hybridization of RNA blots was according to the Gene Screen Plus manual in 1 M NaCl, 10% dextran-sulphate, 1% SDS supplemented with 100 μg/ml salmon sperm DAN for 40 h at 65° C. Blots were washed three times with 2×SSC 1% SDS at 65° C. and once with 0.1×SSC, 1 SDS at room temperature.

The potato GBSS cDNA was isolated from a cDNA library established from poly A+RNA from potato tubers using a maize waxy (GBSS) cDNA as probe. Subcloning of the cDNA in plasmid pUC9 yielded plasmids pW×1.1 (5'-end of the potato GBSS cDNA, and pW×1.3 (3'-end of the potato cDNA (Hergersberg)) and pGB6 (pUC 18 with the two EcoRI cDNA fragments from pW×1.1 and pW×1.3). These plasmids were isolated as described (Birnboim et al. *Nucl. Acids Res.* 7:1513–1523 (1979)). The cDNA inserts, to be used as probes, were isolated by EcoRI or BamHI (pGB6) restriction followed by agarose gel electrophoresis and the 'freeze squeeze' method.

Probes were labelled by random primed directed synthesis with $α^{32}PdCTP$ to high specific activity according to Feinberg and Vogelstein (Feinberg et al.).

Transformation of Potato

Inoculum preparation of Agrobacterium cells carrying the antisense or sense constructs, inoculations of stem segments of *S. tuberosum* PD007 and isolation of binary vector-transformed hairy roots were as described (Visser et al. 1989a). Callus induction n hairy roots, followed by the subsequent regeneration of shoots was as described previously (Visser et al. 1989a). Plants grown in vitro were transferred to the greenhouse to obtain soil-grown tubers.

Plant Materials

In vitro shoot cultures of the *Solanum tuberosum* clones PD007 (HH 578, 2n=2x=24), Ri007 (pBI121 transformed PD007, 2n=2x=24; Visser et al. 1989a, b) and the doubled amf mutant (2n=2x=24; Hovenkamp-Hermelink et al. 1987) were used. The shoots were grown at 21° C. with a regime of 14 h light (3200 lux) per day on basal MS medium (Murashige and Skoog 1962) supplemented with 30 g/l sucrose.

Standard Methods and Reagents

Standard techniques of DNA manipulation were performed as described by Maniatis et al. (1982). All DNA-mediated transformations were carried out with *Escherichia coli* strains JM83 (Vieira and Messing 1982) and MH1 (Casadaban and Cohen 1980). Plasmid isolation was according to Birnboim and Doly (1979) and inserts were isolated from the restriction enzyme-digested plasmids using the "freeze-squeeze" method (Tautz and Renz 1983). Plant DNA was isolated according to Dellaporta et al. (1983). DNA blot hybridizations and radioactive labelling of the isolated 1.3 kb GBSS cDNA fragment from pGB6 (FIG. 1) were as described previously (Visser et al. 1989 b,c,d). Enzymes required for the DNA constructions were from Gibco-BRL and/or Boehringer Mannheim and were used according to the manufacturers' recommendations.

Construction of Vectors

Figure 1:
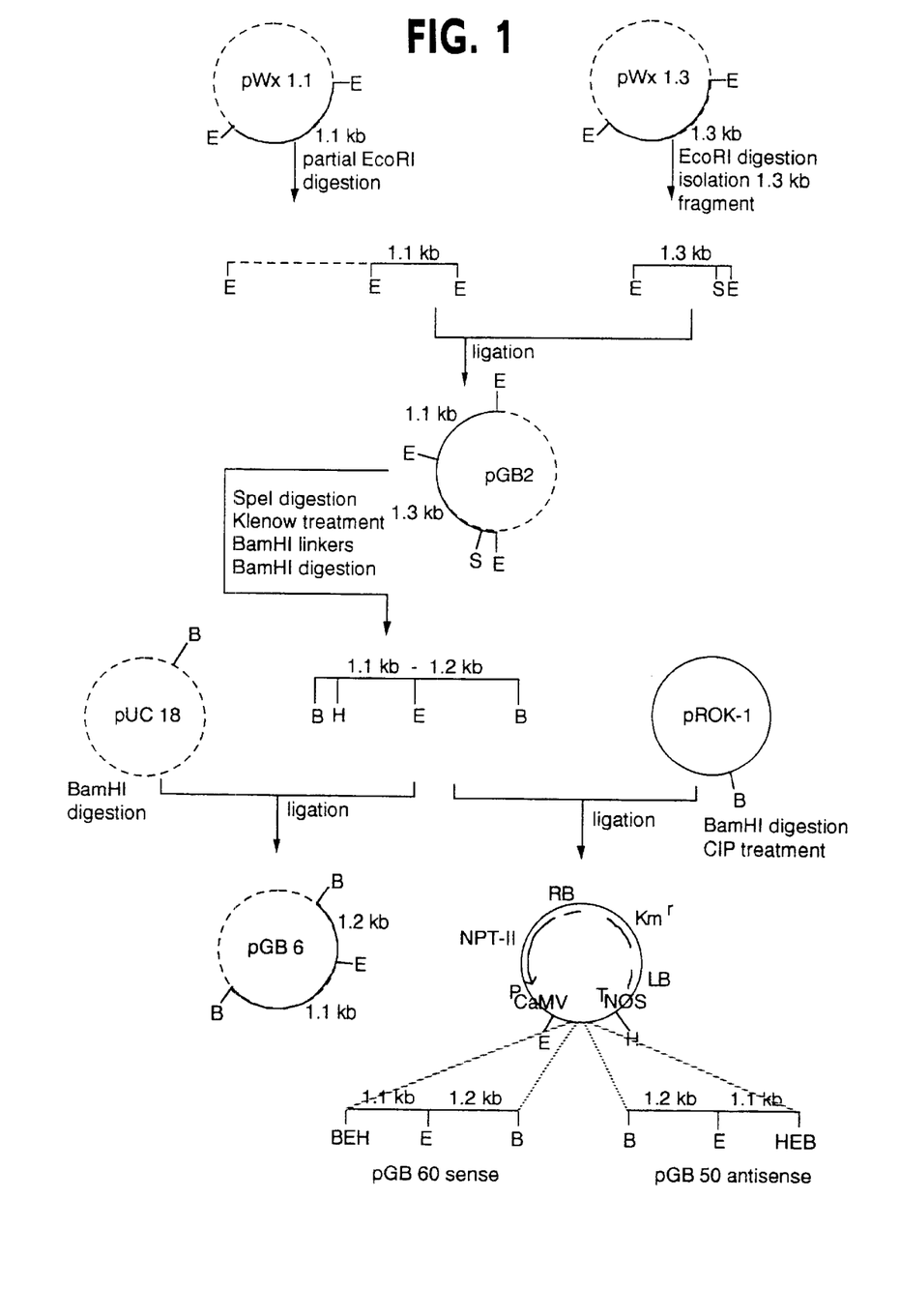

Two subclones encompassing a full-length cDNA clone from potato GBSS isolated from a lambda NM1149 library (Hergersberg 1988; Visser et al. 1989d) were used as indicated in FIG. 1 for the construction of the antisense and sense binary vectors. The antisense (pGB50) and sense (pGB60) vectors obtained after the ligation of the 2.3 kb cDNA in the alkaline phosphatase-treated BamHI site of the binary plant transformation vector pROK-1 (Baulcombe et al. 1986) were introduced into *Agrobacterium rhizogenes* LBA 1334 (Offringa et al. 1986) as described by Visser et al. (1989a). Verification of the integrity of the plasmids in Agrobacterium was as described previously (Visser et al. 1989a).

Iodine Staining of Hairy Roots

Starch granules in root cap cells were stained with a 1:1 (v/v) mixture of Lugol and chloral hydrate as previously described by Jacobsen et al. (1989).

Assays for Amylose Content and GBSS Activity

The amylose/amylopectin ratio in starch from potato tubers was determined by the method described previously (Hovenkamp-Hermelink et al. 1988). By using the equation postulated there: P=(3.5–5.1 R)/(10.4 R-19.9) where R is the ratio of the absorbance at 618 nm and 550 nm, the amylose fraction (P) can be easily determined. Since, when P was calculated for artificial mixtures of amylose and amylopectin of known composition, slight deviations were found between the calculated ratio and the actual ratio, a correction factor was used based on the ratio of calculated and actual values of P in these artificial mixtures. Stock solutions of amylose and amylopectin were made as described by Hovenkamp-Hermelink et al. (1988), mixed to obtain starch solutions containing 0% to 40% amylose and diluted with water to obtain final starch concentrations of 6.25 mg/100 ml.

GBSS activity was measured in 50 μl assay buffer containing 1.0–2.0 mg of enzymatically active starch granules using $^{14}C$-labelled ADP-glucose as substrate, as described by Vos-Scheperkeuter et al. (1986). Suspensions were incubated for 30 min and 90 min at 37° C. to get a linear incorporation of $^{14}C$-ADP-glucose.

Gel Electrophoresis and Immunoblotting

Proteins were extracted from starches as described by Vos-Scheperkeuter et al. (1986). Analysis on 10% SDS polyacrylamide gels and subsequent immunoblotting or silver staining of proteins were performed as described by Vos-Scheperkeuter et al. (1986) and Hovenkamp-Hermelink et al. (1987).

Results

Transformation, Hairy Root Isolation and Shoot Regeneration

Wild-type strains of *A. rhizogenes* and those harboring the antisense (pGB50) and sense (pGB60) DNA constructs of GBSS (FIG. 1) were used to inoculate stem segments of wild-type *S. tuberosum* PD007. *A. rhizogenes* was used because columella cells of root tips contain starch and because the mutation in GBSS leads to the absence of amylose in columella cells in the amf mutant. Since the presence of amylose can be easily monitored by staining hairy roots with iodine (starch staining blue when amylose is present and reddish-brown when amylose is absent), this provides an easy screening method.

Hairy roots, when induced and grown on kanamycin-free medium were obtained in about 10 days after inoculation. Numerous root tips of untransformed PD007 shoots and hairy roots obtained on PD007 stem segments after inoculation with wild-type and pGB60 *A. rhizogenes* strains were tested for their starch composition in columella cells. These preparations always contained blue staining starch when stained with Lugol's solution. Roots inoculated with pGB50 could be classified into three staining groups, i.e. blue, intermediate and reddish-brown. In the intermediate class blue and red staining columella cells were found within the same root tip. Over 50% of the pGB50 inoculated roots showed an altered starch composition, staining either intermediate or red with iodine (Table 1).

To study intra-clone variation 10 root clones, which were established on kanamycin-containing medium, were investigated for starch composition every fortnight during 6-weeks (Table 2). It was found that the antisense effect occurred at a high frequency, but mostly in an unstable fashion. Young root clones with red staining amylose-free starch in the columella cells tended to change into intermediate ones and at a later time after inoculation changed again into amylose-containing, homogeneously blue staining root clones. Although one red root clone appeared to be stably amylose-free, the majority of the root clones was unstable for this antisense effect. All these observations clearly demonstrated that antisense effects for this character could be obtained in columella cells of root tips of transformed potato, but that suppression of amylose synthesis is unstable in such root tips.

Because of the instability problems it was decided to regenerate plants, irrespective of the antisense effect in their columella cells, from kanamycin-resistant hairy roots containing vector T-DNA in order to investigate these effects in other starch-containing parts of transgenic plants. Hairy roots transformed with pGB50 were isolated from stem segments and cultured on medium containing 50 mg/l kanamycin and 200 mg/l claforan. After two more rounds of subculturing, hairy root clones which still grew on kanamycin-containing medium were considered transformed. Each independently derived hairy root was subcultured separately on MS 30 medium with claforan and kanamycin to increase root mass. Root pieces obtained from 46 independently transformed PD007 hairy root clones (designated WA 500 to WA 546) were transferred to callus induction medium. All root clones formed callus, and shoot regeneration was observed in 25 (=54%) of the WA clones. Of these 16 were analyzed further; after in vitro multiplication 5 plants from each of these 16 clones, as well as control plants (pBI121 transformed PD007 and untransformed PD007 plants), were transferred to the greenhouse and soil-grown tubers were harvested.

Tuber Starch Analysis

From all 16 clones subterranean tubers were harvested. Two to three randomly picked tubers from every plant were cut in slices and the cut surfaces were stained with Lugol's solution. Based on the staining reaction three classes were discerned. Eleven plants formed tubers with red staining (amylose-free) starch and three plants formed tubers with only blue staining (amylose-containing) starch, whereas two formed tubers with a mixed staining type of starch. The mixed staining tubers were different from the intermediate staining root tips in that individual cells, which were grouped in a certain zone of the tuber, contained either red or blue staining starch. All tubers from such plants were of mixed staining phenotype. The sizes of the blue and red zones varied. Always the heel side of the tuber (the side attached to the stolon) contained blue staining starch.

Analysis of isolated starch from tubers of the three different staining classes revealed that activity and/or amount of GBSS protein were affected in all the different plants transformed with antisense constructs. Table 3 shows that all plants staining red for tuber starch, which were investigated for those characters, had strongly decreased GBSS activities comparable to that of the amf mutant, whereas all plants with only blue staining tuber starch had significant GBSS activities, which, however, were lower than that of the wild type PD007. The GBSS activity in pBI121 transformed Ri007 plants was equal to that of the wild type. The amylose/amylopectin ratio was determined in tuber starch and the apparent percentage of amylose was calculated. The relative amylose content of tubers with blue staining starch was in some transgenic plants comparable to that of the wild type, PD007 or Ri007, while in other plants it was much lower. In tubers with red staining starch the amylose level of the amf mutant was achieved. The mixed staining tubers had amylose percentages which varied between those seen for the tubers with red and blue staining starch respectively, mainly because these tubers consisted of a mixture of amylose-free and amylose-containing starch.

Figure 2C:
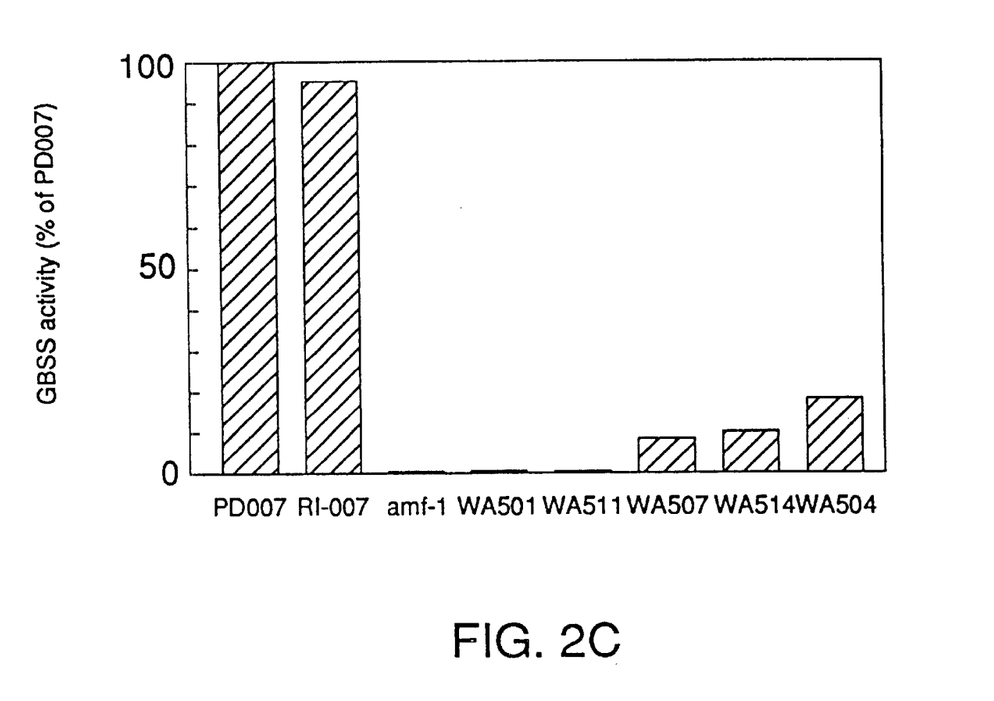
Figure 2D:
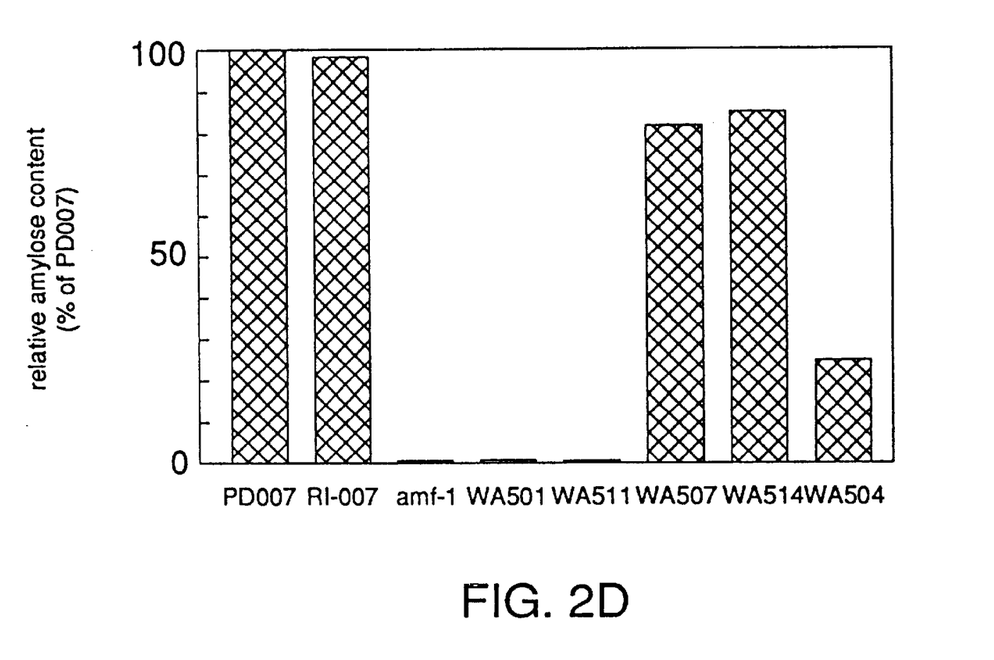

The results are also shown in FIG. 2C and 2D to facilitate a comparison with the heterologous transformants. As can be seen in FIG. 2C, two out of the three different classes of tubers from homologous transformants contained GBSS activities which correspond with their color when stained with Lugol's solution. Levels similar to that of the amf-mutant for red staining tubers and detectable but clearly lower than wildtype GBSS activities for blue staining tubers. The amylose content for these two classes is also in agreement with the color of the tubers (FIG. 2D). No amylose for the red staining tubers and rather high amylose contents comparable to those found in wildtype tubers for the blue staining tubers. The latter group also closely resembles the heterologous transformants. Starches isolated from the 'intermediate' coloring class gave a completely different result. An example of such a transformant is WA504, which has a higher GBSS activity than both transformants from the 'blue colouring' class, WA507 and WA514, but the apparent amylose content of this transformant is much lower than that of the other two transformants.

GBSS protein analyses were performed by running protein extracts from a number of tuber starch samples on SDS polyacrylamide gels followed by subsequent silver staining of the gels or by transferring them onto nitrocellulose filters and immunoblotting with antibodies raised against GBSS from potato. From both silver stained gels or from the immunoblots it is evident that only blue and intermediate staining tubers contain GBSS protein in their starch granules. Although the extraction of protein from starch is difficult to quantify it seems that in the blue staining tubers little reduction of the level of GBSS protein has occurred. As demonstated by the weaker signal on the immunoblot for clones WA 504 and WA 517, a reduced level of GBSS protein is clearly found in the intermediate staining tubers.

Molecular Analysis of the Transformants

Southern blot analyses were performed to determine the number of correctly introduced antisense GBSS constructs in the transgenic plants. Genomic DNA from a number of independently obtained transformants was isolated and digested with EcoRI and BglII. These restriction endonucleases excise the construct in such a way that the number of different bands corresponds to the number of different integrations. In this way it was found that the number of integrations in the independent transformants varied from 1 to 5. In untransformed PD007 or pBI121 transformed plants only the hybridization pattern from the resident GBSS genes could be discerned. No relationship was found between the antisense effects and the number of integrated copies. Both plants with tubers with red or blue staining starch could contain either one or more than one antisense copy.

Stability of Expression of the Antisense Genotype

The antisense GBSS gene is expressed and the antisense-derived phenotype is visible, as is the amf phenotype, in all tissues where starch is formed; apart from columella cells of root tips and tubers this also includes stomatal guard cells. However, although the composition of the starch in the tuber of a given plant seemed to be quite stable, there was always a variable expression of the antisense genotype in stomatal guard cells and in columella cells. Root tips and guard cells with red and with blue staining starch could be found in one and the same plant, irrespective of its tuber starch reaction. The only variability in tuber starch color was found in the transformants with mixed staining starch. These always had a varying zone of blue and red staining starch in their tubers; no variegated patterns or differently oriented zones were ever observed in the mixed staining tubers. Vegetative propagation of tubers with red staining starch from three transformants showed that the antisense trait is transmitted after multiplication and thus is apparently stably integrated into the genome.

Discussion

In this example we describe effects of the introduction of GBSS antisense constructs into potato on the amount and activity of GBSS and on the amylose/amylopectin ratio in potato starch.

Analysis of the hairy roots revealed that the introduction of pGB50 antisense constructs resulted in phenotypic changes, which did not occur when pGB60 sense constructs were used, as judged by the staining of starch in columella cells with Lugol's solution. However, because of the instability of the observed effect in columella cells this system is only suitable for testing constructs for their potential biological effects. Therefore, plants were regenerated from kanamycin-resistant roots irrespective of the root tip phenotype with respect to starch composition. In contrast to the hairy root clones investigated which were mostly blue staining, all but three plants formed tubers with stably red (11 plants) staining starch. None of the investigated transgenic plants, not even the blue ones, had a GBSS activity which was comparable to that of the wild type controls. In this respect the antisense approach was successful in all kanamycin-resistant plants.

The fact that variable expression of the antisense genotype occurs in stomatal guard cells, in which transitory or metabolic starch is deposited, as well as in columella cells of root tips is difficult to explain. Since such metabolic starch, at least in leaves, contains less amylose than reserve starch (Hovenkamp-Hermelink et al. 1988), it might be expected that an effect could be accomplished more easily in leaves. Since less amylose and less GBSS mRNA (Visser et al. 1989) are present a suppressing effect in leaves would be more likely and would also be more stable. If the starch in roottips were also of metabolic origin identical results would be expected. However, our results contradict this expectation. In the guard cells of leaves the results obtained could point to the involvement of a physiological component such as photosynthesis, in roots such an involvement is more difficult to imagine. Another reason for the differences between effects obtained in tubers and in other organs of the plant can perhaps be found in the more constant expression of GBSS mRNA in tubers. The promoter used in this study could also be the reason for the observed phenomenon. The 35S CaMV promoter is considered a constitutive promoter in all tissues, but reports from Benfey and Chua (1989) and Benfey et al. (1989) have shown that this need not always be true. There are at least two domains in the promoter region (Benfey et al. 1989) which, when introduced separately into transgenic plants, can confer different developmental and tissue-specific expression patterns. In our case the complete 35S CaMV promoter perhaps allows specific expression levels in various tissues at different times during the day like those reported for the two different domains of the 35S CaMV promoter (Benfey et al. 1989). More research in the field of variable expression is necessary before one can hope to explain the observed results.

Here, however, we can only draw conclusions from the results derived from tuber starch analysis, since only in tuber starch does the expression appear to be stable and is measurable quantitatively. The data show a reduction of GBSS activity in all the investigated transgenic plants. In those cases where there is total absence of GBSS activity, GBSS protein and amylose are also absent. In all other cases there is an inhibitory effect on activity and possibly also on the amount of GBSS protein. The effect of a lower GBSS activity on the amylose/amylopectin ratio is not straightforward, as was also seen in heterologous GBSS antisense experiments (Visser 1989). The strong reduction in GBSS activity required to evoke only a rather small reduction in the amylose/amylopectin ratio in transformants WA 507 and WA 514 are in contrast to that found in transformant WA 516, which has a higher GBSS activity but a lower amylose content. The interpretation of the effect on amylose/amylopectin ratio is complicated further by the fact that no data on absolute amounts of starch are available.

The introduction of antisense GBSS constructs clearly has an effect on a number of related parameters in starch metabolism. The fact that there is variation among different plants transformed with the same antisense construct is not surprising. Similarly variable responses of plants to particular antisense constructs have also been obtained for antisense chalcone synthase (CHS) in *Petunia hybrida* and *Nicotiana tabacum* (van der Krol et al. 1988), antisense chloramphenicol acetyl transferase in tobacco (Delauney et al. 1988) and antisense polygalacturonase (PG) in tomato (Smith et al. 1988). Moreover, in the animal systems variable inhibition of the target genes by antisense vectors has also been observed (Holt et al. 1986).

It is assumed that the variations in response arise from differential influence on antisense expression of the chromosomal region in which it is integrated, i.e. so-called position effects (van der Krol et al. 1988; Smith et al. 1988). All GBSS antisense transformed plants contained variable numbers of integrated antisense constructs, but no relationship between GBSS copy number and the observed antisense effect could be found. These results are similar to those observed by Van der Krol et al. (1988), where there was no correlation between antisense CHS copy number, antisense CHS mRNA level and phenotypic effects on flower pigmentation. These results differ from those obtained using heterologous GBSS constructs in potato (Visser 1989) where a correlation was found between GBSS copy number and phenotypic effect. A relationship between copy number and antisense effect was also found for antisense polygalacturonase genes in tomato (Schuch et al. 1989) and for antisense chloramphenicol acetyl transferase (CAT) in constitutively expressing chloramphenicol acetyltransferase (CAT$^+$) tobacco plants (Delauney et al. 1988).

In conclusion, this example shows that the introduction of GBSS antisense cDNA constructs results in a strongly reduced GBSS activity, which in most cases is accompanied by an equally large reduction in the amount of GBSS protein and amylose content. However, in those cases where the antisense effect is not absolute the degrees of reduction in the amount of GBSS activity, GBSS protein and the amylose content are unpredictable. The antisense approach can be a very effective alternative technique to mutagenesis programs for enzymes involves in the metabolic pathway of starch formation, especially in vegetatively propagated (polyploid) crops. Moreover, the availability of antisense plants should make normally recessively inherited mutations more easily obtainable, because antisense genes themselves act as dominant (hemizygous) suppressor genes, thus enabling plant breeders to shorten their breeding programs.

TABLE 1

Iodine staining of starch in columella cells of hairy roots formed on stem segments of *Solanum tuberosum* PD007 after inoculation with *Agrobacterium rhizogenes* pGB50.

| Experiment | No. of roots stained | Percentages of roots staining |  |  |
|---|---|---|---|---|
|  |  | Blue | Intermediate | Red |
| I | 43 | 40 | 21 | 39 |
| II | 49 | 41 | 21 | 38 |
| III | 103 | 34 | 33 | 34 |
| IV | 34 | 41 | 18 | 41 |
| V | 78 | 33 | 31 | 36 |
| Total | 319 | 38 | 24 | 38 |

TABLE 2

Iodine staining behavior of starch in columella cells of kanamycin-resistant hairy roots containing pGB50 and analysed over a period of 42 days.

| Root clone | Days after oculation |  |  |  |
|---|---|---|---|---|
|  | 1 | 15 | 30 | 42 |
| 1 | R → | R → | R → | R |
| 2 | R → | R* I → | B → | I B |
| 3 | I → | R* I B → | I* B → | I B |
| 4 | I → | I* B → | B → | B |
| 5 | B → | B → | B → | B |
| 6 | R → | I → | R* I → | I |
| 7 | R → | R → | R* I B → | I B |
| 8 | I → | R* I → | I* B → | I B |
| 9 | I → | B → | I* B → | I B |
| 10 | B → | B → | B → | B |

R, red staining; I, intermediate staining; B, blue staining.

For every measurement obtained 3–8 root tips were stained. Of root clones with different staining root tips the clones marked with an asterisk were transferred to fresh medium.

TABLE 3

Tuber starch color, GBSS activity and amylose content of antisense GBSS transformed potato plants and their controls.

| Plant clone | Tuber starch color after iodine staining | GBSS activity | Apparent amylose content |
|---|---|---|---|
|  |  | (as % of the content of PD007) |  |
| Class I |  |  |  |
| WA 501 | red | 0 | 0 |
| WA 505 | red | 3 | 2 |
| WA 506 | red | 0 | 2 |
| WA 508 | red | 0 | 2 |
| WA 511 | red | 0 | 0 |
| WA 512 | red | 2 | 3 |
| Class II |  |  |  |
| WA 504 | blue/red | 18 | 26 |
| WA 517 | blue/red | 6 | 22 |
| Class III |  |  |  |
| WA 507 | blue | 9 | 83 |
| WA 514 | blue | 10 | 84 |
| WA 516 | blue | 32 | 49 |
| Controls |  |  |  |
| PD007 | blue | 100 | 100 |
| Ri007 | blue | 96 | 106 |
| amf | red | 0 | 0 |

The tuber starch color was determined by staining a cross-section of a tuber with Lugol's solution as described in the Materials and methods. GBSS activities measured as the incorporation rate of $^{14}$C-labelled ADP-Glucose, ranged from 0 to 8.1 pmol/min per mg starch in individual tubers with red staining starch, from 8.7 to 70 pmol/min per mg starch in individual tubers with blue staining starch and from 6.2 to 32.7 pmol/min per mg starch in individual tubers with mixed staining starch. The values of untransformed or pBI121 transformed PD007 ranged from 66.9 to 98.9 pmol/min per mg starch and for the amf mutant were approx. 0 pmol/min per mg starch. Amylose percentages varied from 0% to 1.9% for tubers with red staining starch, from 14% to 27% for tubers with blue staining starch and from 5% to 7% for tubers with mixed staining starch. Transgenic plant clones WA 502, WA 503, WA 509, WA 513 and WA 515, all containing red staining tuber starch, were regarded as class I transformants but were not included in the above analysis.

EXAMPLE 2

This example investigates if it is possible to increase the amylose content in potato tubers. This might be achieved by overexpressing granule-bound starch synthase if this enzyme is rate limiting to amylose biosynthesis. In order to investigate this question a full length genomic, actively transcribed (Visser et al. 1989, van der Leij et al. 1991), GBSS gene was introduced in a number of different wildtype and heterozygous (Amfamf) potato genotypes. The results of these experiments show that no significant increase of the amylose content could be obtained in any of the transformants. Surprisingly it was found that the introduction of this gene can instead block the expression of both the introduced and endogenous GBSS genes.

Materials and Methods
Plant Materials

In vitro shoots of the *Solanum tuberosum* genotype cv. Astarte (2n=4x=48), PD 007 (HH 578, 2n=2x=24), the Amfamf genotype 871024-2 (2n=2x=24) and the amfamf genotype 871029-31 (2n=2x=24, Jacobsen et al. 1989) were used. The shoots were grown at 21° C. with a regime of 14 h light per day on basal MS medium (Murashige and Skoog 1962) supplemented with 30 g/l sucrose (MS 30).

Standard Methods and Reagents

Standard techniques of DNA manipulation were performed as described by Maniatis et al. (1982). Plasmid DNA isolations from *Escherichia coli* were according to Birnboim and Doly (1979) and inserts were isolated from the restriction enzyme digested plasmid using the method described by Tautz and Renz (1983). Enzymes were from Gibco/BRL or Boehringer Mannheim and were used according to the manufacturers recommendations.

Construction of Vectors and Transformation of Potato

The construction of the binary plasmid pWAM 100 containing a full length GBSS genomic gene, capable of complementing an amylose-free mutant, was described before (van der Leij et al. 1991). The construction of the binary plasmid pWAM 100 is as follows: The lambda EMBL4 derivative LGBSS$^{wt}$-6 (Visser et al. 1989 a; see also FIG. 2) was used as source of the genomic GBSS gene for cloning in the binary vector pBIN19 (Bevan, *Nucleic Acids Res.*, 12:8711–8721 1984). The 6.5-kb GBSS gene fragment, obtained after digestion with BglII, was ligated into the BamHI site, resulting in the recombinant plasmids pWAM 100. In pWAM 100, the GBSS gene is oriented in the opposite direction towards the plant kanamycin resistance gene. The binary plasmid was introduced into *Agrobacterium rhizogenes* LBA 1334 using triparental mating (Visser et al. 1991b). The binary vector pWAM 100 was also introduced into *Agrobacterium tumefaciens* LBA 4404 using the direct transformation method of competent Agrobacterium cells described by Höfgen and Willmitzer (1988). Integrity of the plasmids in Agrobacteria was verified according to Holmes and Quigly (1981).

Potato stem segments were inoculated with *A. rhizogenes* as described by Visser et al. (1989a). The formation of hairy roots was allowed to take place on solid MS 30 medium with 200 mg/l cefotaxim, without kanamycin. Regeneration of shoots from hairy roots was as described before (Visser et al. 1989a). Transformation of potato stem segments with *A. tumefaciens* followed by subsequent regeneration of shoots from these explants was as described by Visser (1991).

Microtubers were obtained by transferring nodal buds to MS medium containing high amounts of sucrose (80 g/l) as described by Hovenkamp-Hermelink et al. (1987).

Plants grown in vitro were transferred to the greenhouse to obtain soil-grown tubers.

Screening of Tubers

Subterranean tubers obtained from *A. rhizogenes* or *A. tumefaciens* transformants (respectively R-n or T-n) were cut and the surface was stained with Lugols solution.

Assays for GBSS Activity and Amylose Content

GBSS activity was measured in 50 µl assay buffer containing samples of 1–2 mg of enzymatically active starch as described by Vos-Scheperkeuter et al. (1986) using $^{14}$C labelled ADP-glucose as substrate.

The amylose/amylopectin ratio in starch from potato tubers was determined by the method described previously (Hovenkamp-Hermelink et al. 1988).

Gel Electrophoresis and Immunoblotting

Proteins were extracted from starches as described by Vos-Scheperkeuter et al. (1986). Analysis on 10% SDS polyacrylamide gels and subsequent immunoblotting or protein staining were performed as described by Vos-Scheperkeuter et al. (1986) and Hovenkamp-Hermelink et al. (1987).

Southern and Northern Analysis

DNA of greenhouse grown plants was isolated from young leaves according to Dellaporta et al. (1983) and digested with the restriction enzymes EcoRI and BglII. Southern blot hybridizations with radioactive labelled GBSS cDNA was performed as described previously (Visser et al. 1989b,d).

RNA isolation from tubers and leaves, followed by northern blotting and hybridization were as described (Visser et al. 1989d).

Results

The diploid genotype PD007 and the tetraploid cv. Astarte were used in transformation experiments using the *Agrobacterium rhizogenes* strain harboring the binary vector pWAM100.

The diploid genotype 871024-2 was used in transformation experiments harbouring the vector pWAM100. Table 4 shows the number of individual transformants obtained using either transformation approach.

The transformants were allowed to tuberize in the greenhouse. All *A. tumefaciens* transformants produced tubers whereas only 65% of the *A. rhizogenes* transformants produced tubers. From all tubers starch was isolated to determine amylose/amylopectin ratio and from most of the tuber starch samples also the GBSS activity was measured (Table 5).

From the results of Table 5 it is obvious that none of the transformants had a significantly higher amylose content as compared to the wildtype controls. However, both in the *A. rhizogenes* and the *A. tumefaciens* transformants clones were found containing red staining starch in their tubers. Also in the case of the tetraploid cv Astarte where 12 transformants produced tubers (Table 4), one clone was found with red staining sectors in the tubers (results not shown). This was also the case in one of the 871024-2 transformants (T-21). In all transformants with red staining tuber starch the GBSS activity proved to be very low or undetectable. In these particular transformants no detectable amounts of amylose could be measured (Table 5, clones R-11, R-30a and T-40), thus resembling the amf-mutant for these characters.

The phenotype from these transformants in other starch containing tissues was different from that of the amf-mutant; stomata and roottips had blue and only occasionally red staining starch. In this respect these transformants resembled more some anti-sense GBSS transformed clones (Visser et al. 1991a).

These results were due to the fact that transformants contained extra copies of the GBSS gene, as was confirmed both by polymerase chain reaction experiments as well as by Southern blot analysis. The number of integrated copies varied from one to four per haploid genome and no relation between copy number and inhibitory effect was found (results not shown).

Discussion

In this example, the effect of the introduction of additional homologous GBSS gene copies in diploid (both heterozygous and homozygous for the amylose-free character, respectively Amfamf and AmfAmf) and tetraploid potatoes on GBSS activity and amylose percentage is investigated.

Although it was the intention to increase expression of the GBSS gene leading to an increased activity of the enzyme, something which was reported for sense alfalfa glutamine synthetase in transgenic tobacco (Eckes et al. 1989) no such phenomenon was observed in our experiments. Unexpectedly the introduction of extra copies of the GBBS gene led to a (almost) complete inhibition of the GBSS enzyme activity in 8% to 22% of the transformants (Table 5), irrespective of their ploidy level or genetic constitution for the amf-character which in the heterozygous diploid means that only one copy of the gene has to be suppressed to achieve an effect. The lower or absent GBSS activity was accompanied with lower amounts or total absence of GBSS protein when analyzed by Western blot (cf. Table 5). The absence of GBSS protein and activity in turn led to an almost complete absence of amylose (<1% of the wildtype level) and could be made visible by staining cut tuber surfaces with Iodine: presence of amylose gave blue staining, absence of amylose red staining starch (Table 5).

The phenomenon that a mutant phenotype can be obtained after introduction of one or more copies of a wildtype gene in a wildtype host has been described before (Napoli et al 1990, Smith et al. 1991) and is known as co-suppression. One common feature of co-suppression in different plant systems seems to be the occurrence of instable or reversible phenotypes. An indication for this phenomenon in the five sense GBSS transformants showing an effect in the tuber, might be the starch composition in other starch containing organs of these plants. Another example of such an unstable or reversible phenotype might be transformant T-21 which contained partly blue and red staining starch in its tuber. It is thought that these phenotypes are related to natural cases of gene expression like flower color patterning, and epigenetic effects as in paramutations and other modulating mechanisms of transposition (Jorgensen 1991, Matzke and Matzke 1991).

At present two explanations for the feature of co-suppression are in favor: methylation or anti-sense RNA effects. Methylation is thought to be a result of interactions of homologous sequences at different sites in the genome. Several examples which share similarities with co-suppression are known to be related to methylation. In these cases homology between promoters seems to be essential and suppression acts at the level of transcription (Matzke et al. 1989, Matzke and Matzke 1991). In our case homology with the complete sequence including the promoter region with resident sequences exists. However, none of the 12 potato clones transformed with a chimaeric gene consisting of the GBSS promoter and the β-glucuronidase (GUS) gene contained amylose-free starch (Visser et al. 1991b, unpublished results).

A second explanation for co-suppression involves the so called anti-sense RNA interaction. It was postulated by Grierson et al. (1991) that anti-sense RNA could be generated because of simple read through of the kanamycin resistance gene which is cotransferred for selection and used sofar in all the systems known to show the phenomenon of co-suppression (van der Krol et al. 1990, Napoli et al. 1990, Grierson et al. 1991, Matzke and Matzke 1991). However, the fact that the GBSS promoter, which was used in our case, is a much more powerful promoter than for instance the 35S (CaMV) promoter (Visser et al. 1991b) makes this unlikely. Rather the place of integration, also known as position effect, seems to play a more important role. It is known from experiments with promoterless constructs that most of the integrations take place in regions of the genome which are trancriptionally active (Koncz et al. 1989, Goldsbrough and Bevan 1991). In potato about 10% of the plants transformed with a promoterless GUS-gene showed GUS activity in tubers and/or leaves.

According to this example, additional copies of the structural gene granule-bound starch synthase (GBSS) were transferred into different potato genotypes using either *Agrobacterium tumefaciens* or *Agrobacterium rhizogenes* as a vector to investigate the possibility of increasing the amylose content in potato tubers. Out of eighteen transformants, only two had a higher GBSS expression, but this did not lead to increased amounts of amylose in tuber starch. Surprisingly, however, in five transformants a strongly reduced GBSS activity was found. In the three transformants which showed the highest reduction in GBSS activity, this severe reduction was accompanied by the absence of GBSS protein and amylose in the starch granules. The specific inhibition of GBSS expression involved both the introduced and the endogenous gene. The effect obtained was not related to the ploidy level of the plant nor to the number of extra gene copies introduced into the plant.

In conclusion, this example shows that the introduction of an actively transcribed granule-bound starch synthase gene into potato may lead to suppression of the expression of both the introduced and the endogenous gene.

TABLE 4

The number of (tuberizing) transformants obtained either by using A. rhizogenes or A. tumefaciens harboring the binary vector pWAM 100.

| Plant genotype | Bacterium | No. of transformants | with tubers |
| --- | --- | --- | --- |
| PD007 | R | 19 | 9 |
| Astarte | R | 16 | 12 |
| 871024-2 | T | 30 | 30 |

R = A. rhizogenes, T = A. tumefaciens

TABLE 5

Comparison of GBSS activity, presence of GBSS protein, amylose content and starch color of pWAM 100 transformants with the untransformed controls (PD007, 871024-2 and 871029-31)

| Plant | GBSS activity as % of wt* | Amylose content as % of wt** | GBSS protein | Tuber starch color |
| --- | --- | --- | --- | --- |
| PD007 (AmfAmf) | 100 | 100 | + | blue |
| R-5 | nd | 84 | + | blue |
| R-6 | nd | 86 | + | blue |
| R-11 | 0 | <1 | − | red |

TABLE 5-continued

Comparison of GBSS activity, presence of GBSS protein, amylose content and starch color of pWAM 100 transformants with the untransformed controls (PD007, 871024-2 and 871029-31)

| Plant | GBSS activity as % of wt* | Amylose content as % of wt** | GBSS protein | Tuber starch color |
|---|---|---|---|---|
| R-19 | nd | 79 | + | blue |
| R-20 | nd | 86 | + | blue |
| R-24 | 129 | 102 | + | blue |
| R-27 | nd | 73 | + | blue |
| R-29 | nd | 95 | + | blue |
| R-30a | 4 | 0 | − | red |
| 871024-2 (Amfamf) | 100 | 100 | + | blue |
| T-4 | 18 | 75 | + | blue |
| T-7 | 131 | 95 | + | blue |
| T-11 | 49 | 75 | + | blue |
| T-13 | 46 | 95 | + | blue |
| T-21 | 10 | 30 | − | red/blue |
| T-25 | 81 | 100 | + | blue |
| T-26 | 56 | 95 | + | blue |
| T-34 | 44 | 95 | + | blue |
| T-40 | 3 | 0 | − | red |
| 881029-31 (amfamf) | 0 | 0 | − | red | nd = not determined
GBSS protein presence determined by Western blot analysis, + = present, − = absent
*PD007 and 87 1024-2 activity ranged from 65 to 100 pMol/min/mg starch, 871029-31 activity from 0 to 4 pmol/min/mg starch
**PD007 amylose % 18 to 27%
871024-2 amylose % 18 to 24%
871029-31 amylose % 0 to 4%

REFERENCES

Baulcombe D C, Saunders G R, Bevan M W, Mayo M A, Harrison B D (1986) Nature 321:446–449
Benfey P N, Chua N-H (1989) Science 244:174–181
Benfey P N, Ren L, Chua N-H (1989) EMBO J 8:2195–2202
Birnboim H C, Doly J (1979) Nucleic Acids Res 7:1513–1523
Casadaban M J, Cohen S N (1980) J Mol Biol 138:174–207
Delauney A J, Tabacizadeh Z, Verma D P S (1988) Proc Natl Acad Sci USA 85:4300–4304
Dellaporta S L, Wood J, Hicks J B (1983) Plant Mol Biol Reports 1:19–21
Eckes P, Schmitt P, Daub W, Wengenmayer F (1989) Mol Gen Genet 217:263–268
Goldsbrough A, Bevan M (1991) Plant Mol Biol 16:263–269
Grierson D, Fray R G, Hamilton A J, Smith C J, Watson C F (1991) Trends Biotechnol 9:122–123
Hergersberg M (1988) Inaugural Dissertation, Köln
Höfgen R, Willmitzer L (1988) Nucleic Acids Resarch 16:9877
Holmes D S, Quigley M (1981) Anal Biochem 114:193–201
Holt J T, Gopal T V, Moulton A D, Nienhuis A W (1986) Proc Natl Acad Sci USA 83:4794–4798
Hovenkamp-Hermelink J H M, Jacobsen E, Ponstein A S, Visser R G F, Vos-Scheperkeuter G H, Bijmolt E W, de Vries J N, Witholt B, Feenstra W J (1987) Theor Appl Genet 75:217–221
Hovenkamp-Hermelink J H M, de Vries J N, Adamse P, Jacobsen E, Witholt B, Feenstra W J (1988) Potato Res 31:241–246
Jacobsen E, Hovenkamp-Hermelink J H M, Krijgsheld H T, Nijdam H, Pijnacker L P, Witholt B. Feenstra W J (1989) Euphytica 44:43–48
Jorgensen R (1991) Trends Biotechnol 8:340–344
Koncz C, Marini N, Mayerhofer R, Koncz-Kalman Z, K örber H, Redei G P, Schell J (1989) Proc Natl Acad Sci USA 86:8467–8471
van der Krol A R, Lenting P E, Veenstra J, van der Meer I M, Koes R E, Gerats A G M, Mol J N M, Stuitje A R (1988) Nature 333:866–869
van der Krol A R, Mur L, Beld M, Mol J N M, Stuitje A R (1990) The Plant Cell 2:291–299
van der Leij F R, Visser R G F, Oosterhaven K, van der Kop D A M, Jacobsen E, Feenstra W J (1991) Theor Appl Genet 82:289–295
Maniatis T, Fritsch E F, Sambrook J (1982) Molecular cloning: A laboratory manual, Cold Spring Harbor Laboratory, Cold Spring Harbor, N.Y.
Matzke M A, Priming M, Trnovsky J, Matzke A J M (1989) EMBO J 8:643–649
Matzke Ma, Matzke A J M (1991) Plant Molec Biol 16:821–831
Murashige T, Skoog F (1962) Physiol Plant 15:473–497
Napoli C, Lemieux C, Jorgensen R (1990) The Plant Cell 2:279–289
Offringa I A, Melchers L S, Regensburg-Tuink A J G, Costantino P, Schilperoort R A, Hooykaas P J J (1986) Proc Natl Acad Sci USA 83:6935–6939
Schuch W, Bird C R, Ray J, Smith C J S, Watson C F, Morris P C, Gray J E, Arnold C, Seyman G B, Tucker G A, Grierson D (1989) Plant Mol Biol 13:303–312
Sheehy R E, Kramer M, Hiatt W R (1988) Proc Natl Acad Sci USA 85:8805–8809
Shure M, Wessler S, Fedoroff N (1983) Cell 35:225
Smith C J S, Watson C F, Ray J, Bird C R, Morris P C, Schuch W, Grierson D (1988) Nature 334:724–726
Smith C J S, Watson C F, Bird C R, Ray J, Schuch W, Grierson D (1991) Mol Gen Genet 224:475–481
Tautz D, Renz M (1983) Anal Biochem 132:14–19
Vieira J, Messing J (1982) Gene 19:259–268
Visser R G F (1989) Manipulation of the starch composition of *Solanum tuberosum* L, using *Agrobacterium rhizogenes* mediated transformation, PhD Thesis, University of Groningen
Visser R G F, Jacobsen E, Witholt B, Feenstra W J (1989a) Theor Appl Genet 78:594–600
Visser R G F, Hesseling-Meinders A, Jacobsen E, Nijdam H, Witholt B, Feenstra W J (1989b) Theor Appl Genet 78:705–714
Visser R G F, Jacobsen E, Hesseling-Meinders A, Schans M J, Witholt B, Feenstra W J (1989c) Plant Mol Biol 12:329–337
Visser R G F, Hergersberg M, van der Leij F R, Jacobsen E, Witholt B, Feenstra W J (1989d) Plant Sci 64:185–192
Visser R G F (1991) Plant Tissue Cultur Manual (Lindsy K, ed), Kluwer Academic Publishers, B5:1–9
Visser R G F, Somhorst I, Kuipers G J, Ruys N J, Feenstra W J, Jacobsen E (1991a) 225:289–296
Visser R G F, Stolte A J, Jacobsen E (1991b) Plant Mol Biol 17:691–699
Vos-Scheperkeuter G H, de Boer W, Visser R G F, Feenstra W J, Witholt b (1986) Plant Physiol 82:411–416

What is claimed is:

1. A transgenic potato plant which, as a result of genetic engineering has a genome containing at least one gene construct containing a full length potato granule-bound starch synthase (PGBSS) cDNA or genomic DNA sequence coding for PGBSS in reverse orientation in an expression cassette which is functional in potato plants, said gene construct giving rise to tubers containing essentially amylose free starch; wherein said expression cassette comprises in the 5'-3' direction of transcription: an upstream promoter base sequence, a base sequence for transcription into mRNA under control of said upstream promoter base sequence comprising coding and template strands, and a downstream transcription terminator base sequence, wherein the coding strand of said base sequence for transcription comprises an inverted sequence of bases complementary to a run of bases of PGBSS mRNA, wherein the transcript of said base sequence for transcription substantially inhibits the expression of PGBSS.

2. The transgenic potato plant according to claim 1 wherein said upstream promoter sequence is the cauliflower mosaic virus 35S promoter ($P_{CaMV}$).

3. The transgenic potato plant according to claim 1 wherein said upstream promoter sequence is the PGBSS promoter.

4. The transgenic potato plant of claim 1 wherein said terminator is nopaline synthase terminator ($T_{nos}$).

5. The transgenic potato plant of claim 1 wherein said terminator is PGBSS terminator.

6. The potato plant of claim 1, wherein said gene construct contains the neomycin phosphotransferase II gene (NPT-II) kanamycin resistance marker.

7. A tuber of the potato plant of claim 1.

8. The transgenic potato plant of claim 1 wherein said construct contains full length PGBSS cDNA.

Figure 3A:
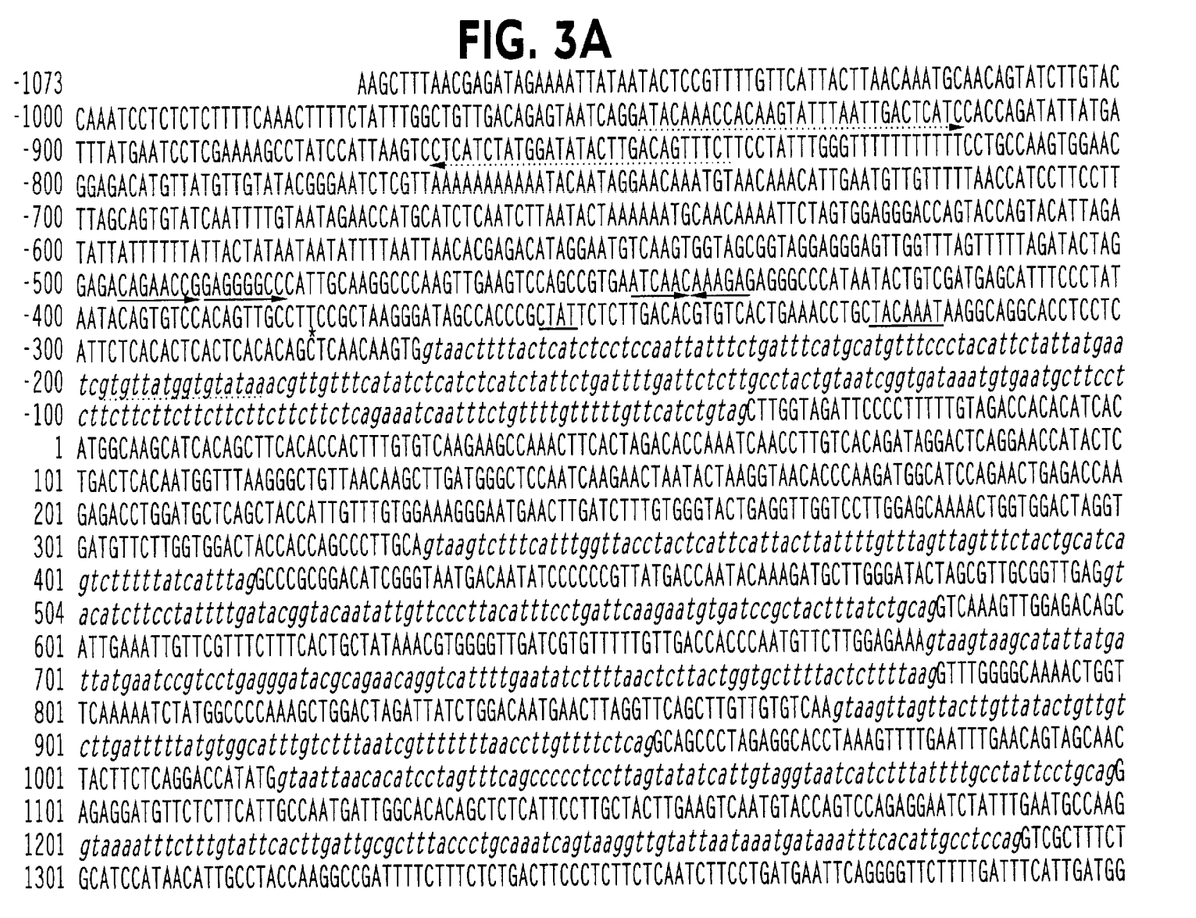
FIG. 3 is the complete genomic nucleotide sequence of the potato granule-bound starch synthase (GBSS) gene with the translational start of nucleotide +1. The stop codon at position 2961 is shown in bold. Introns are shown in small italics, bordered by bold type. The putative promoter sequences and polyadenylation signals are underlined, poly (A) addition sites are marked with asterisks. The start of the largest cDNA is marked with a black dot. The sequence around the start of transcription is underlined with a dashed line. G-box like sequences are overlined with arrows and large imperfect inverted repeats with dashed arrows.
Figure 3B:
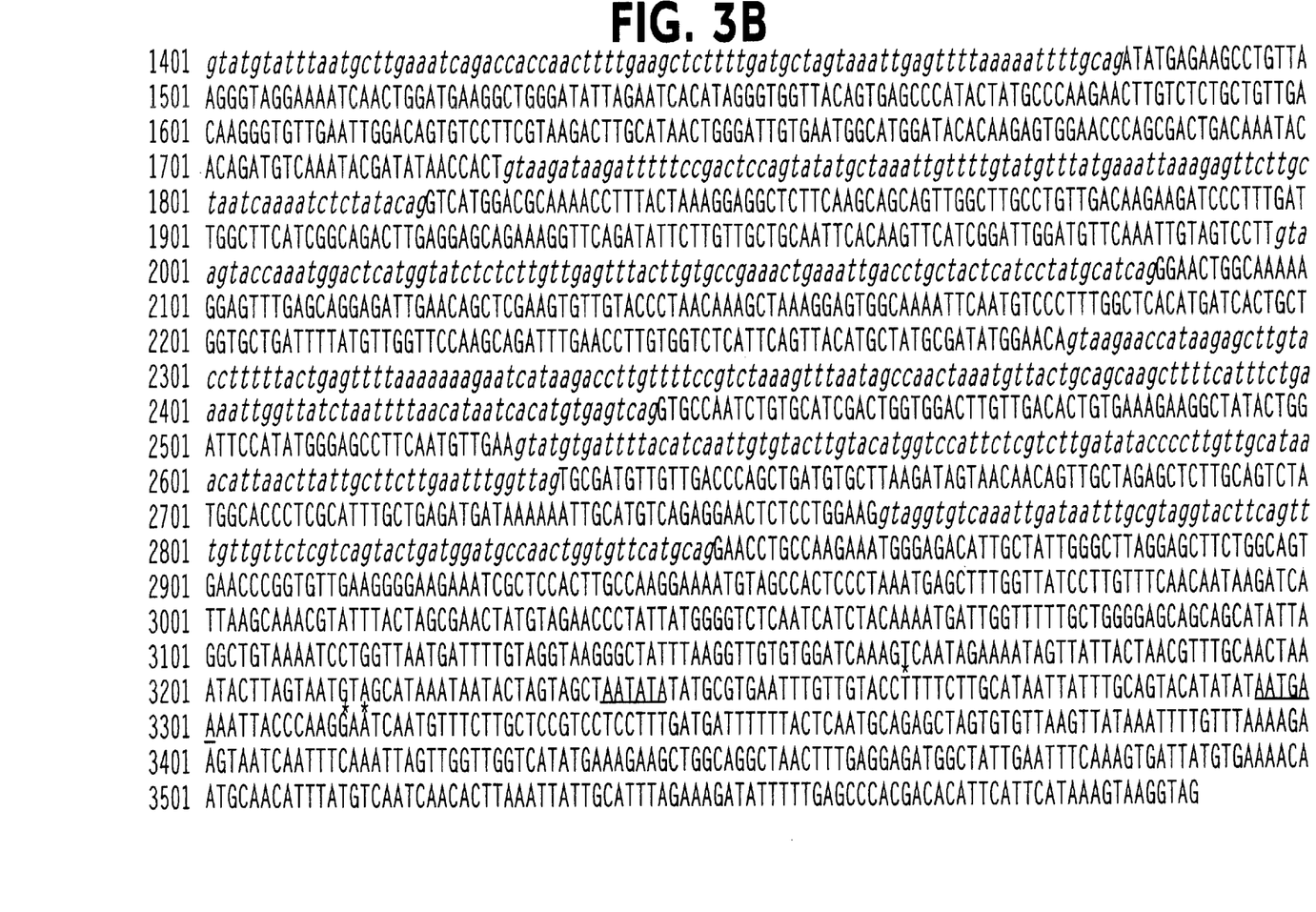

9. The transgenic potato plant of claim 1 wherein said base sequence for transcription comprises a sequence of bases complementary to the sequence as set forth in FIG. 3.

10. A method for producing a transgenic potato plant exhibiting at least one modified phenotypic trait by inhibiting the expression of an endogenous gene, said method comprising:

integrating into the genome of the plant cell at least one gene construct containing a full length potato granule-bound starch synthase (PGBSS) cDNA or genomic DNA sequence coding for PGBSS in reverse orientation in an expression cassette which is functional in potato plants comprising in the 5'-3' direction of transcription: an upstream promoter base sequence, a base sequence for transcription into mRNA under control of said upstream promoter base sequence comprising coding and template strands, and a downstream transcription terminator base sequence functional in said cell wherein a transformed cell is obtained; and growing said transformed plant cell, wherein the coding strand of said base sequence for transcription comprises an inverted sequence of bases complementary to a run of bases of PGBSS mRNA, wherein the transcript of said base sequence for transcription substantially inhibits the expression of potato granule-bound starch synthase.

11. The method according to claim 10 wherein said construct further comprises T-DNA.

12. The method according to claim 10 wherein upstream promoter sequence is CaMV 35S promoter.

13. The method according to claim 10 wherein upstream promoter sequence is PGBSS promoter.

14. The method according to claim 10 wherein said terminator is nopaline synthase terminator.

15. The method according to claim 10 wherein said terminator is potato granule-bound starch synthase terminator.

16. The method according to claim 10 wherein the gene construct was integrated into the potato genome by transformation with Agrobacterium selected from a group consisting of Agrobacterium rhizogenes and Agrobacterium tumefaciens.

17. The transgenic potato plant according to claim 1 further comprising variable numbers of integrated gene construct.

18. The method according to claim 10, further comprising integrating variable numbers of gene construct in the transformed plants.

19. The method according to claim 18, wherein there is no correlation between the number of PGBSS genes integrated copies and phenotypic effect.

20. A process for producing essentially amylose-free starch, said process comprising:

obtaining a potato cell which has been transformed by introducing into the genome of the potato cell at least one gene construct containing a full length potato granule-bound starch synthase (PGBSS) cDNA or genomic DNA sequence coding for PGBSS in reverse orientation in an expression cassette which is functional in potato plants, said expression cassette comprising in the 5'-3' direction of transcription: an upstream promoter base sequence, a base sequence for transcription into mRNA under control of said upstream promoter base sequence comprising coding and template strands, and a downstream transcription terminator base sequence functional in said cell, wherein the coding strand of said base sequence for transcription comprises an inverted sequence of bases complementary to a run of bases of PGBSS mRNA, wherein the transcript of said base sequence for transcription substantially inhibits the expression of PGBSS;

growing the transformed potato cell to produce a potato plant containing potato tubers;

producing at least one potato from said potato tubers; and separating starch from said potato, wherein said starch is essentially amylose-free.

21. The process for producing essentially amylose-free starch according to claim 20, wherein said upstream promoter sequence is the cauliflower mosaic virus 35S promoter ($P_{CaMV}$).

22. The process for producing essentially amylose-free starch according to claim 20, wherein said upstream promoter sequence is the PGBSS promoter.

23. A construct containing a full length potato granule-bound starch synthase (PGBSS) cDNA or genomic DNA sequence coding for PGBSS in reverse orientation to a promoter, said construct giving rise to tubers containing essentially amylose-free starch.

* * * * *